(12) United States Patent
Subramanyan et al.

(10) Patent No.: US 6,524,242 B2
(45) Date of Patent: Feb. 25, 2003

(54) NON-CONTACT METHOD FOR MEASURING AMOUNT OF SEBUM OR OIL ON SUBSTRATE IN REAL TIME USING FLUORESCENCE DYE

(75) Inventors: Krishna Kumar Subramanyan, Clifton, NJ (US); Leonard Van Gorkom, Englewood, NJ (US); Zhenhe Zhu, deceased, late of Peekskill, NY (US), by Xi Yuan Zhu, Legal Representative; Archana K Sah, Quincy, MA (US); Thomas Hancewicz, Ringwood, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/884,396

(22) Filed: Jun. 19, 2001

(65) Prior Publication Data

US 2003/0004404 A1 Jan. 2, 2003

(51) Int. Cl.[7] .................................................. A61B 5/00
(52) U.S. Cl. ........................................ 600/306; 600/310
(58) Field of Search ................................ 600/306, 310, 600/473, 476, 478

(56) References Cited

U.S. PATENT DOCUMENTS

| 4,224,950 | A | | 9/1980 | Bore et al. | |
| 4,313,393 | A | | 2/1982 | Barbuscio et al. | |
| 4,423,736 | A | * | 1/1984 | DeWitt et al. | ............... 600/306 |
| 4,480,921 | A | * | 11/1984 | Leveque et al. | ............ 356/434 |
| 5,094,248 | A | | 3/1992 | Kawam | |
| 5,760,407 | A | * | 6/1998 | Margosiak et al. | ....... 250/461.1 |

FOREIGN PATENT DOCUMENTS

| JP | 02220630 | 9/1990 |
| JP | 05060686 | 3/1993 |
| JP | 09292214 | 11/1997 |
| WO | 96/25884 | 8/1996 |

* cited by examiner

Primary Examiner—Stephen M. Hepperle
(74) Attorney, Agent, or Firm—Ronald A. Koatz

(57) ABSTRACT

The invention provides a non-contact (non-invasive) method for measuring quantity of sebum oil on skin or other substrate. The method includes applying fluorescent lipophilic dye to the substrate site of interest, illuminating the site at the excitation wavelength of the dye, and collecting fluorescent emission of desired wavelength of the dye. Because the measurements are truly non-contact, they can be made in real time on the same sites for any desired length of time.

13 Claims, 4 Drawing Sheets

NON-CONTACT METHOD FOR MEASURING AMOUNT OF SEBUM OR OIL ON SUBSTRATE IN REAL TIME USING FLUORESCENCE DYE

FIELD OF THE INVENTION

The present invention relates to non-contact methods for measuring quantity of sebum or oil on skin or other substrates. While measurement can be done in vivo or ex vivo, the technique is preferred for use in vivo because of the ability to measure formation of oil on the skin in real time.

BACKGROUND OF THE INVENTION

Methods of analyzing the quantity of sebum or oil produced on substrate/surfaces using so-called contact techniques are known. Generally such contact methods mean that the measurement involves contact with the surfaces where the sebum/oil is being measured. Since the sebum or oil is generally sampled and then measured, it is difficult or impossible to monitor changes in real time, i.e., as they are occurring. For example, "In-vivo infrared analysis of the recovery of sebaceous lipids after dilapidation", J. Invest. Dermatology, 112(4), 779 (1999), N. Kolliar et al. describe an ATR-FTIR method for sebum detection using a fiber optic probe attachment. This is a contact method involving collection and transfer of sebum onto an ATR (attenuated total internal reflection device) crystal. Other contact methods include use of sebutape, use of a sebumeter and lipid extraction using solvents.

JP 09292214 (assigned to Sekisui Chemical) discloses a non-contact ultrasound method for measuring skin sebum. Here however, the ultrasound measures only the thickness of the fat layer and not actual amounts of sebum produced.

Other contact methods are also disclosed in the following references.

In JP 05060686, sebum is collected from the surface using a plate and then an IR spectrum is obtained using ATR device.

In JP 02220630, sebum quantity is measured using IR rays to detect reflected light from sebum collecting surface.

In U.S. Pat. No. 5,094,248 to Kawam, sebum is collected onto a hydrophilic open celled microporous polymeric film by patching to skin, and the amount of sebum collected is measured against a selected background by optical methods.

In U.S. Pat. No. 4,224,950 to Bore et al., sebum is collected onto a frosted glass plate and quantified using optional methods.

In U.S. Pat. No. 4,313,393 to Barbuscio et al., sebum is collected using an oil absorbent material, and the amount collected is quantified using a dye.

In WO 96/25884 (assigned to Courage & Khazaka), sebum secretion on skin is measured using a microporous water repellent, sebum absorbing opaque foil which absorbs sebum and changes in transparency.

None of these methods are true "non-contact" methods and, therefore, they do not allow monitoring sebum levels in vivo in real time.

Unexpectedly, applicants have discovered that it is possible to measure quantity of sebum or oil in vivo using non-contact technique. This also allows real time measurement.

BRIEF DESCRIPTION OF INVENTION

The present invention relates to a non-contact (non-invasive) method for measuring quantity of sebum or oil on skin or other substrate. Because the measurements are truly non-contact, they can be made in real time on the same sites for any desired length of time.

The present invention discloses one specific embodiment for non-contact measurement. A second embodiment is disclosed in a separate application filed on same day as the subject application.

In the embodiment of the present invention, an amount of sebum (or oil) is measured by choosing a desired spot on the subject's body; optionally cleansing the spot by a mild wash using a cleanser or wipe; applying a desired amount of fluorescent dye (e.g., octadecyl fluorescent or "ODF", a highly lipophilic fluorescent dye) to the spot; illuminating the spot at the excitation wavelength of the fluorescent dye (470 nm for ODF); and acquiring an image at the desired wavelength of the dye (525–540 nm for ODF). Alternatively fluorescence spectral measurement (e.g., in steps (4) & (5) noted below) can be acquired from the spot at the appropriate excitation wavelength using, for example, a fiber optic probe assembly attached to a spectrophotometer.

More specifically, the invention comprises a non-contact process or method for measuring sebum or oil from skin or other substrate comprising:

(1) choosing a desired spot (e.g., on the forehead), typically about 1–2 cm in diameter (could be as large as the entire forehead), on the body of a subject;

(2) optionally cleansing said spot using typically mild cleansing wash, facial wash or alcoholic wipes in an amount adequate to remove all or part of sebum or oil;

(3) applying lipophilic fluorescent dye, which exhibits concentration dependent self-quenching, at levels just above its self quenching concentration (5 to 10 $\mu g/cm^2$ for ODF) to the spot where sebum oil is to be measured;

(4) illuminating the spot on said subject at the excitation wavelength of the fluorescent dye (e.g., 450–500 nm for ODF); and (5) collecting fluorescent emission at desired wavelength of the dye (e.g., 525–560 for ODF) using for example a camera and suitable image acquisition system.

In an alternative embodiment, the fluorescence spectra of the dye on the spot may be recorded by using a fiber optic probe attached to a spectrophotometer. The fiber optic probe delivers the illumination from the light source to the spot (again at 450–500 nm for ODF) and also collects the fluorescence from the spot (e.g., at 525–560 nm for ODF)); and (6) quantifying data from acquired image by analyzing fluorescence intensity in the images or spectra and converting to amount of sebum or oil increased using appropriate calibrations determined in separate experiments.

Images or spectra are acquired at desired time intervals and converted to oil or sebum amounts using step (6) in the real time, normally in-vivo application of the method. Often it is desired to measure sebum/oil increase from a point where there is little or no previous oil. In this case, the measured skin spot would be cleansed at the beginning (step (2)), dye applied (step (3)) and measurements taken.

However, it should be understood that the measurements can be taken to measure oil/sebum increase at any time, not just the beginning. Thus, at a later point for example, after there has already been sebum/oil collection, it is possible to avoid step (2), apply dye and measure how much oil/sebum has been collected from that later measurement point.

Also, even if measured from beginning, one can skip cleansing step. However, it will be appreciated, that a baseline measurement of oil/sebum should be taken to quantitate.

DETAILED DESCRIPTION OF THE INVENTION

Figure 1:
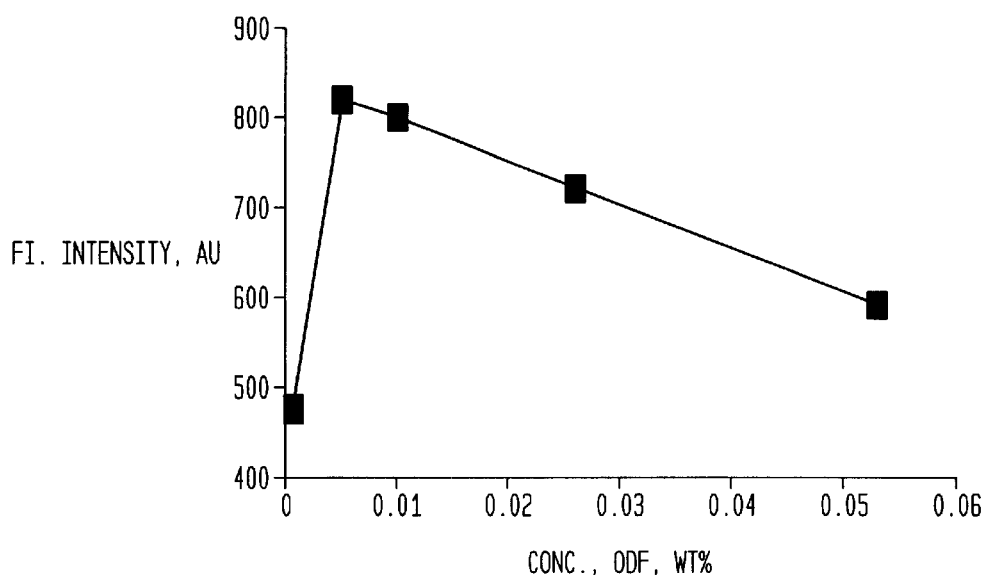
FIG. 1 shows self-quenching of ODF in ethanol solution.

The present invention relates to a non-contact method for measuring quantity of sebum or oil on skin or other substrate, preferably in-vivo. The measurement could be done ex-vivo but the advantage of "real time" measurement would be lost.

Specifically, the invention provides a method for measuring sebum or oil from skin or other substrate (e.g., hair, fabric etc.) in vivo in real time comprising:

(1) choosing a desired spot (e.g., forehead), typically about 1–2 cm in diameter (could be as large as entire forehead) on the body of a subject;

(2) optionally (preferably) cleansing said spot using typically mild cleansing wash or alcohol wipes in an amount adequate to remove all (preferably) or part of sebum or oil;

(3) applying lipophilic (more oil soluble the better) fluorescent dye, which exhibits concentration dependent self quenching concentration (5 to 10 $\mu$g/cm$_2$ for ODF) to the spot where sebum oil is to be measured; and (4) illuminating the spot on said subject at the excitation wavelength of the fluorescent dye (e.g., 450–500 nm for ODF); and (5) collecting fluorescent emission at desired wavelength of the dye (e.g., 525 to 560 nm for ODF) using, for example, a camera and suitable image acquisition system.

(In an alternative embodiment, the fluorescence spectra of the dye on the spot may be recorded by using a fiber optic probe attached to a spectrophotometer. The fiber optic probe delivers the illumination from the light source to the spot (again at 450–500 nm for ODF) and also collects the fluorescence from the spot (e.g., at 525–560 nm for ODF)); and (6) quantifying data from acquired image by analyzing fluorescence intensity in the images or spectra and converting to amount of sebum or oil increased using appropriate calibrations determined in separate experiments.

As noted earlier, while preferred, it is not necessary to record increase in sebum/oil from the beginning and instead measurements can be done at any time. In this regard, a baseline measurement of oil/sebum can be taken at any time (beginning or later) and application of dye and data collection occur from that point forward.

Each of the process steps is discussed in more detail below and in the examples.

As noted, the first step in the non-contact method of measuring sebum or oil on substrate according to the subject invention is to choose a subject and choose a desired spot on the subject suitable for measurement techniques of sebum/oil release.

Preferably, the method is used for measurement of sebum. In general sebum which is a complex mixture of triglycerides, fatty acids, sterols, wax esters and squalene, is secreted by the sebaceous glands and emerges at the surface of the skin via the hair follicles. Sebum build up on skin is associated with facial sheen, lack of cleanliness and in general with the perception of oiliness/greasiness which is an unpleasant sensory trait. The amount of sebum on skin has in the past been directly linked to the perception of oiliness.

A preferred location for sebum production and measurement is the forehead. A typical test site is about 3 cm in diameter. Looking at sites on the right side, left side or center of forehead, typically the center site is preferred as this would typically yield most amount of sebum.

In the optional second step of the process, the desired spot is cleansed or "degreased" by applying the cleanser over the spot and rubbing for about 30 seconds, typically followed by rinsing for about 15 seconds in warm water. Alternatively, the spot can be degreased using a facial wipe or using an absorbent material such as cigarette paper or bentonite clay.

As noted, whether it is desired from beginning to use sebum/oil as baseline or whether getting readings later in the method, it is possible to not degrease at all and simply use oil/sebum present as starting point from which to measure.

In the third step of the invention, the fluorescent dye (i.e., compound which has fluorescent emission at given wave length when solution of it and/or given substrate are excited at defined wavelength) is applied.

A preferred probe is an oil soluble lipophilic dye (the more oil soluble, the better) that exhibits concentration dependent self quenching (decrease in fluorescent intensity due to non-radiative energy transfer) for example octadecyl fluorescent (ODF). The dye is used as probe to trace appearance of, for example, sebum. ODF is a lipophilic membrane probe with very low water solubility. It has a strong emission band at around 525 nm in ethanol when excited at about 470 nm. The emission wavelength shifts to about 540 nm when ODF is dissolved in model sebum. ODF also undergoes self quenching at high concentrations as a result of collision between molecules. FIG. 1 depicts the self-quenching of ODF in ethanol solution. A similar concentration dependent self-quenching is expected in other solvents including model sebum.

After the fluorescent probe is added to skin (or other substrate), an excitation beam is applied to obtain fluorescent images to be acquired and measured.

In steps (4) and (5) of the invention, fluorescence spectra of ODF or other probe in solutions and on skin surface may be obtained using a spectrophotometer (e.g., Perkins Elmer LS50B spectrophotometer) with a fiber optic probe accessory. The fiber optic probe may be gently placed on the skin surface with no excess pressure and held in place using a holder with a fixed gap between the probe surface and the substrate.

The fluorescence images may be acquired, for example, using a multi-frequency variable focus fluorescence imaging system m with a tunable light source. The polychromatic illumination system may consist of a 120W Xenon short arc lamp, which emits broad band light. The light passes through a galvanometric scanner mounted on a grating to make monochromatic light. The wavelengths from this arc in the range of 250–690 nm with a typical bandwidth of 12 nm. The light is directed to the subject area of study using a flexible quartz light guide. The excitation light illuminating the study area may be a few centimeters in diameter, preferably 2 to 4 centimeters, and the region of interest is centered in the middle of the illuminated area.

A 105 mm F2.8 Micro Nikkon Lens was used to collect the emitted fluorescence emulsion. The emission was passed through an LCTF set to the appropriate wavelength and imaged on to a TEA/CCD digital camera from Princeton instruments. Our studies are conducted typically at a magnification of 3–5 ×.

The software package Metamorph by Princeton Instruments allows all camera options to be controlled by the software. In step (c) of the invention, the acquired images are analyzed using this program. Typically the fluorescence intensity of the subject area is measured by tracing the area on the screen and allowing the software to count illumination on a gray scale.

Image Acquisition

For ex-vivo studies, the skin or substrate to be analyzed is mounted on to a flat board and positioned in the excitation beam. For in-vivo studies, the subject's head may be positioned in a head brace placed in front of the camera. Adjustments of the subject's height are achieved by altering the head brace such that the area of interest is in the center of the excitation beam. The camera is moved to focus the image. Typically 16-bit images are acquired using an exposure time of 500 ms. Using ODF as probe on skin, the excitation may set at about 470 nm and the emission is collected at about 565 nm.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

METHODOLOGY

Equipment

Fluorescence spectra of ODF in solutions and/or skin surface were obtained using Perkins Elmer LS50B Spectrophotometer with a cuvette or fiber optic probe accessory as desired. For measuring fluorescence in solutions, solutions were placed in the cuvette and in the path of the excitation beam inside the spectrophotometer. For measuring fluorescence spectrum on skin or other substrate, the fiber optic probe may be gently placed on the skin surface with no excess pressure and held in place using a holder with a fixed gap between the probe surface and the substrate.

Images were obtained, for example, using variable focus fluorescens system with tunable light source. The system, camera and software actually used are as described in the text. Image acquisition is also as described in text above by positioning samples in the path of an excitation beam.

Experimental Procedure

For calibration experiments (on porcine or human skin) an alcoholic solution of model sebum containing ODF was applied to a 4 cm$^2$ area on skin. Typically 4.5 μl of the alcoholic solution is applied carefully over the specified area so that the sebum and ODF are uniformly distributed over the test site. The sebum levels are varied from 0–1000 μg/cm$^2$ while the ODF concentration is constant at 5 μg/cm$^2$. After application of the solution, 1–2 minutes was allowed for the ethanol to evaporate and then an image was captured and the intensity measured.

For the in-vivo regreasing studies the foreheads of subjects were cleaned by wiping twice with alcohol wipes. An alcoholic solution of ODF was applied to a 4 cm$^2$ site in the middle of the forehead such that the ODF concentration on skin is about 5 μg/cm$^2$ (same as that used in the calibration). An image was captured and recorded as the zero time point. The sites on the foreheads were then imaged at various time points (usually 1 hour intervals) and the intensities were measured. The calibration curve is used to convert these intensities into sebum amounts on skin and regreasing plots were obtained.

EXAMPLE 1

Fluorescence of ODF in Solution

ODF solutions in different solvents and surfactant solutions were prepared and their fluorescence characteristics studied. The results are summarized in Table 1.

TABLE 1

Characteristics of ODF Fluorescence in Different Solvents

| Solvent | Excitation | Emission | Rel. Intensity |
| --- | --- | --- | --- |
| Water | 470 | 520 | Very low |
| Ethanol | 470 | 540 | High |
| 2% SLES | 470 | 520–530 | High |
| 2% CAPB | 470 | 530–535 | High |
| Sebum | 470 | 530–540 | High |

As can be seen, ODF has very poor solubility in water and displays weak fluorescence. However, the solubility increases in aqueous surfactant solutions (above CMC) and significant fluorescence emission can be observed. In sebum, ODF has a strong emission at around 540 nm while, in ethanol, emission is also observed at around 525 nm.

FIG. 1 shows the self quenching of ODF in ethanol solution. Similar quenching will be observed in other solvents as well including sebum.

EXAMPLE 2

Fluorescence of ODF on Skin

Figure 2:
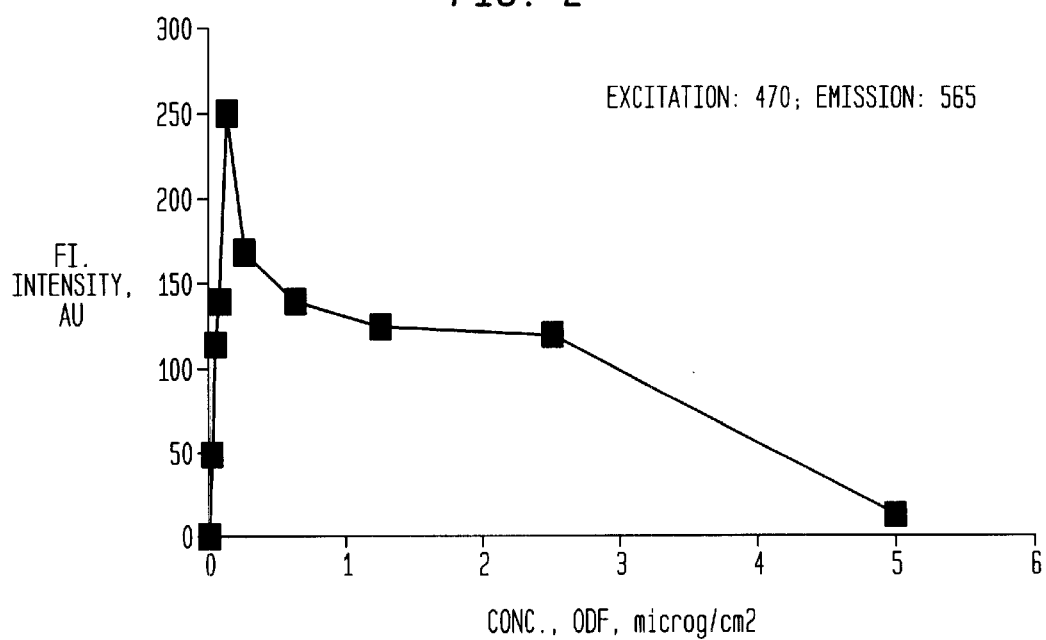
FIG. 2 shows that when ODF is applied to skin, it has concentration dependent self quenching.

Excitation and emission spectra were acquired using the LS50B spectrophotometer with ODF dissolved in sebum applied to porcine skin. The emission from ODF in sebum from skin surface is at around 545 nm when excited at 470 nm. There is no significant auto fluorescence observed under these excitation conditions from the skin. When ODF is applied by itself (no sebum) to skin it displays a concentration dependent self quenching as shown in FIG. 2. The maximum intensity is seen at around 0.3 μg/cm$^2$ ODF concentration and at 5 μg/cm$^2$ all the fluorescence is quenched. All further experiments were conducted with ODF concentration in sebum maintained constant at 5 μg/cm$^2$ when applied to skin.

ODF Fluorescence in Presence of Sebum

Figure 3:
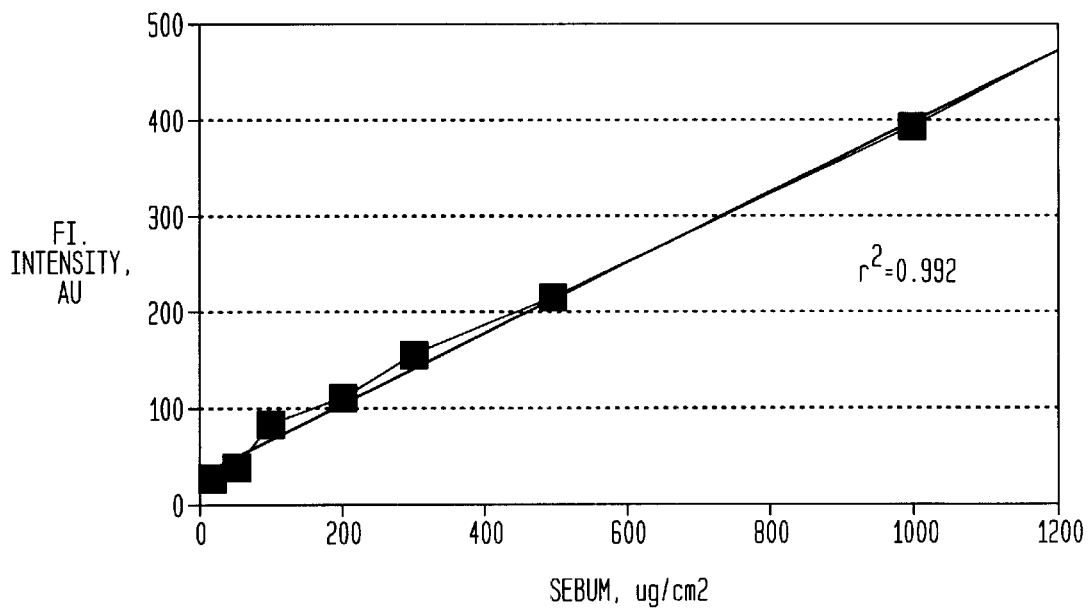
FIG. 3 shows that when sebum is added to ODF, fluorescence intensity increases linearly with amount of sebum (porcine skin was used).

When ODF is applied on skin along with sebum fluorescence is observed at 540 nm when excited at 470 nm. It was mentioned in the previous section that when ODF is applied to clean skin at 5 $\mu$g/cm$^2$ no fluorescence is observed. When sebum is added to the ODF the fluorescence intensity increases due to release of self-quenching. The intensity increases linearly with amount of sebum and is shown in FIG. 3 for porcine skin.

EXAMPLE 3

ODF Calibration on Human Skin

Figure 4:
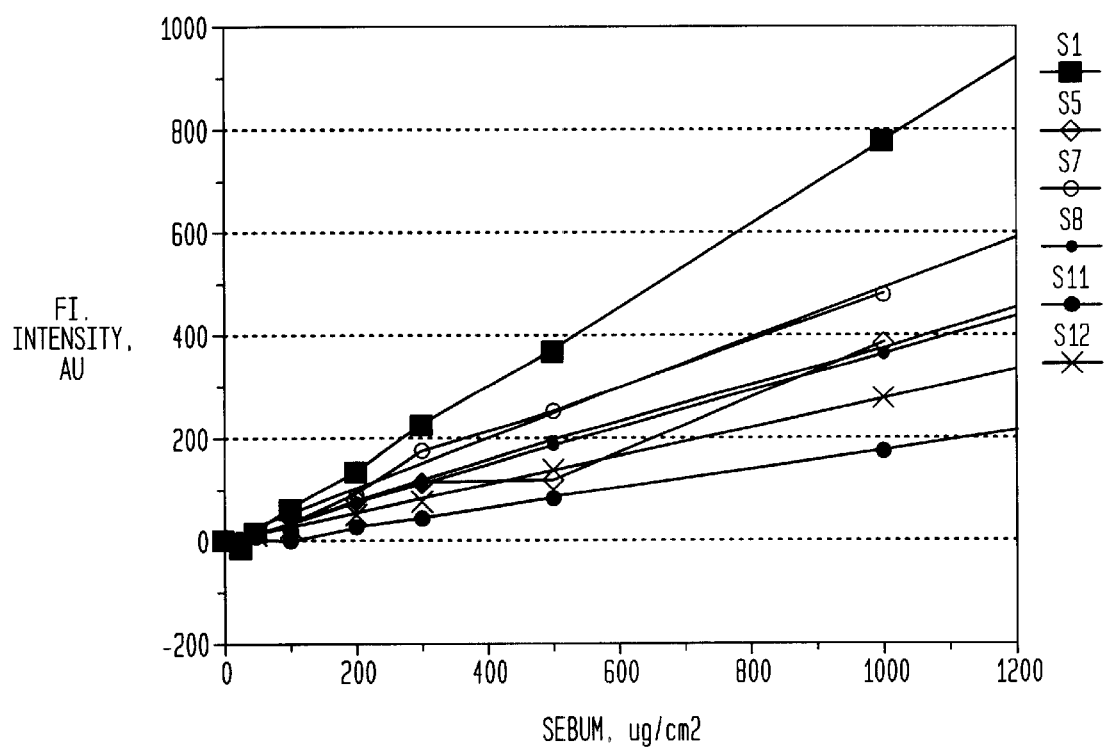
FIG. 4 shows calibration of ODF in sebum on forehead of human subjects.

Solutions containing ODF and sebum in ethanol were applied to a 4 cm$^2$ spot on the forehead. The ODF concentration was constant at 5 $\mu$g/cm$^2$ while the sebum was varied from 0–1000 $\mu$g/cm$^2$. The intensities were measured from the images acquired and the calibration plot shown in FIG. 4. Firstly, it can be seen that the slopes of the calibration lines are different for various subjects. Each calibration line, however is quite linear with r$^2$ values in the range 0.97–0.99.

EXAMPLE 4

Pilot Regreasing Study

Figure 5:
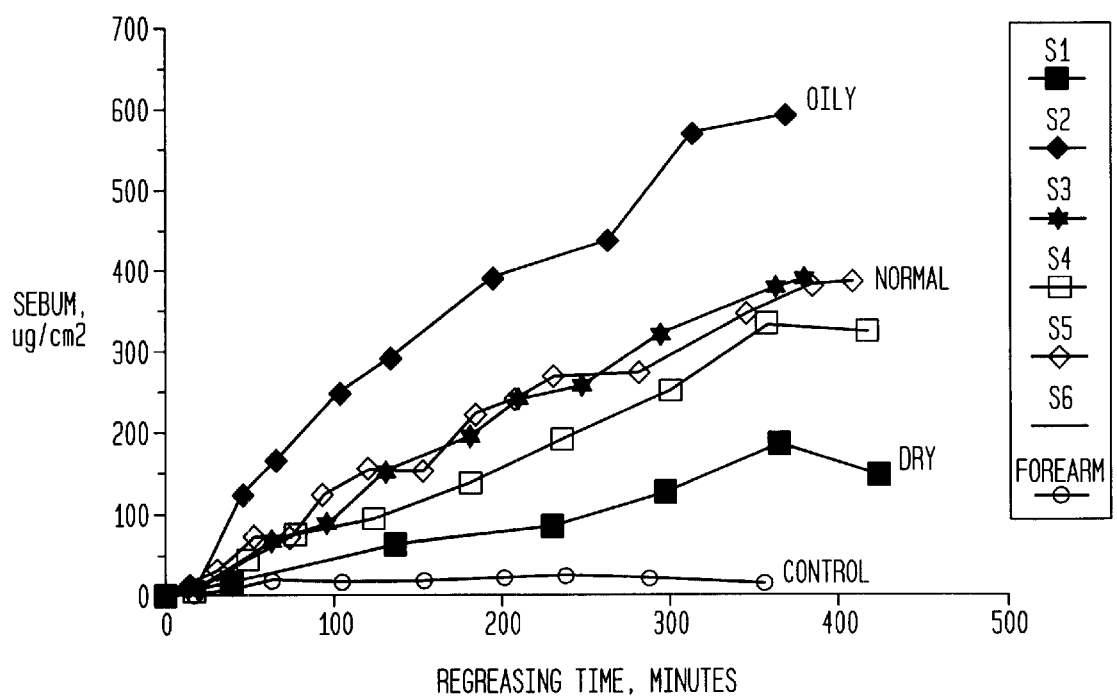
FIG. 5 shows result from regressing plot.
Figure 6:
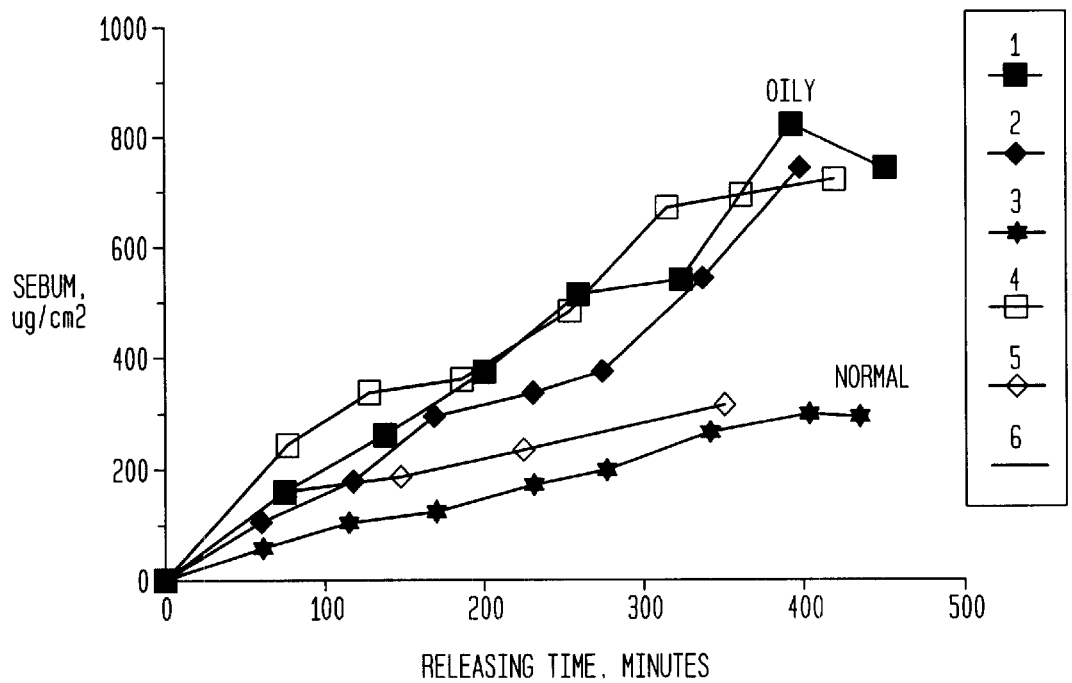
FIG. 6 shows result from regressing plot.

A pilot regressing study was conducted to verify the method using the procedure detailed above. Appropriate calibration plots shown in FIG. 4 were used for each subject and the intensities converted to sebum amounts. The sample images obtained clearly show increase in fluorescence intensity, over time, for all three subjects. In the case of the oily subject it was possible to see sebum (dye) in the cracks and lines on the forehead and at long times even see the flow pattern of the sebum. The regreasing plots are shown in FIGS. 5 and 6. Clearly the regreasing plots seem to fall into three categories: oily, normal and dry. This distinction fits the self-perception of the subjects quite well. As a control in the study images were taken for the same period of ODF applied to a subject's forearm. No increase in intensity was observed at this site as there is hardly any sebum produced on the inner forearm.

In general, this method works on the principle of self-quenching of the fluorophore octadecyl fluorescein (ODF) at high concentrations. The self quenching is released as the fluorophore is diluted and this can be used as a measure of dilution of the probe (proportional to amount of solvent) under well calibrated conditions. Several other fluorophores, such as carboxy fluorescein (water soluble) and Rhodamine chloride exhibit similar quenching behavior.

EXAMPLE 5

Pilot Regreasing Study

Figure 7:
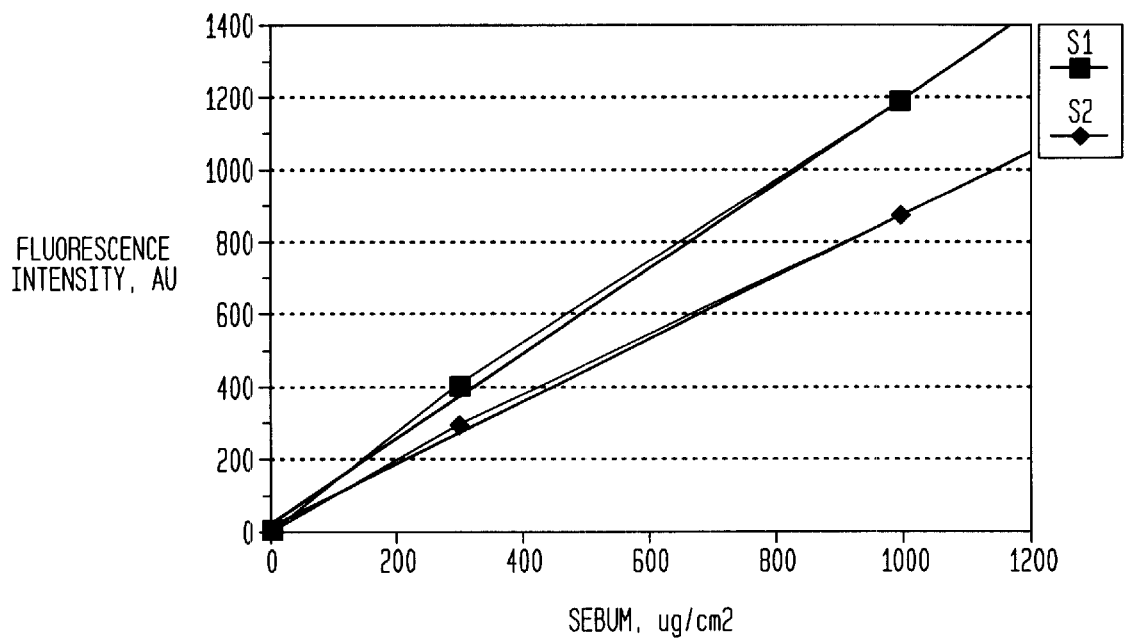
FIG. 7 indicates calibration plot of fluorescence intensity versus sebum amount (fiber optic spectral measurement, human forehead skin).
Figure 8:
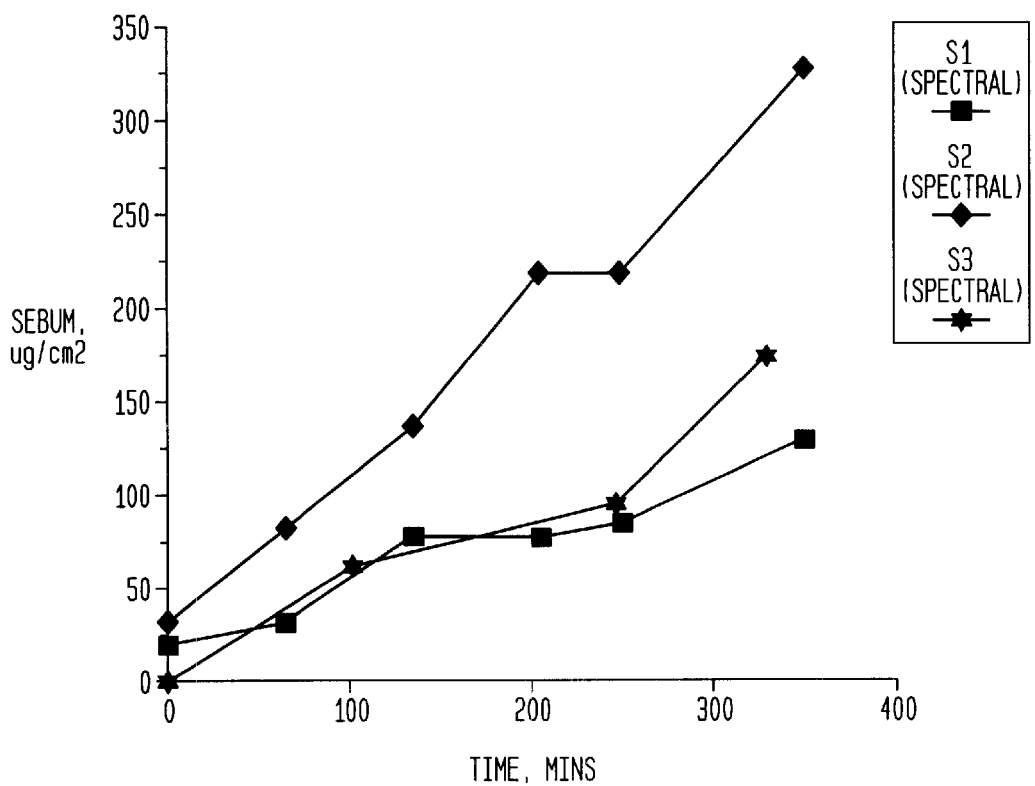
FIG. 8 shows result from regressing plot.

A pilot regressing study was conducted to verify the method using the fiber optic measuring device following the procedure detailed above. Appropriate calibration plots were used (shown in FIG. 7) for each subject to convert the intensities to sebum amounts. The regreasing plots for 3 subjects are shown in FIG. 8.

In general, this method works on the principle of self quenching of the fluorophore octadecyl fluorescein (ODF) at high concentrations. The self quenching is released as the fluorophore is diluted and this can be used as a measure of dilution of the probe (proportional to amount of solvent) under well calibrated conditions. Several other fluorophores, such as carboxy fluorescein (water soluble) and Rhodamine chloride exhibit similar quenching behavior.

What is claimed is:

1. A non-contact process or method for measuring sebum or oil from skin or other substrate comprising:
   (1) choosing a desired spot on the body of a subject;
   (2) optionally cleansing said spot using cleansing wash, facial wash or alcoholic wipe in an amount adequate to remove all or part of sebum or oil;
   (3) applying fluorescent lipophilic dye to the spot where sebum or oil is to be measured;
   (4) illuminating the spot on said subject at the excitation wavelength of the fluorescent dye; and
   (5) collecting fluorescent emission at desired wavelength of the dye.

2. A process according to claim 1, wherein other substrate comprises hair or fabric.

3. A process according to claim 1, wherein said desired spot is on the forehead of said subject.

4. A process according to claim 1, wherein said spot is about 1–3 cm in diameter.

5. A process according to claim 1, wherein there is no cleansing step and amount of oil or sebum is baseline for sebum/oil increase.

6. A process according to claim 5, wherein said baseline sebum/oil measurement of step (2) occurs after steps (3), (4) and (5) have already occurred at least once before.

7. A process according to claim 1, wherein said dye exhibits concentration dependent self quenching.

8. A process according to claim 7, wherein said dye is applied at levels about said self quenching concentration.

9. A process according to claim 8, wherein said dye is octadecyl fluorescein and is applied at levels of 5–10 $\mu$g/cm$^2$.

10. A process according to claim 1, wherein dye is octadecyl fluorescein and excitation wavelength at which spot is illuminated is 450–500 nm.

11. A process according to claim 1, wherein dye is octadecyl fluorescein and wavelength at which fluorescent emission is collected is 525–560 nm.

12. A process according to claim 1, wherein illumination of step (4) is provided by a fiber optic probe.

13. A process according to claim 1, wherein fluorescence of step (5) is collected by a fiber optic probe.

* * * * *